United States Patent [19]

Smith

[11] 4,150,949

[45] Apr. 24, 1979

[54] IMMUNOASSAY FOR GENTAMICIN

[75] Inventor: David S. Smith, London, England

[73] Assignee: Technicon Instruments Corporation, Tarrytown, N.Y.

[21] Appl. No.: 787,654

[22] Filed: Apr. 14, 1977

[30] Foreign Application Priority Data

Apr. 15, 1976 [GB] United Kingdom .............. 15736/76

[51] Int. Cl.² .................... G01N 21/52; G01N 33/16
[52] U.S. Cl. .................. 23/230 B; 23/230 M; 23/915; 195/103.5 A; 424/8; 422/82
[58] Field of Search ........... 23/230 B, 230 M, 253 R; 424/2, 7, 8; 195/103.5 R, 103.5 A

[56] References Cited

U.S. PATENT DOCUMENTS

| | | | |
|---|---|---|---|
| 3,399,972 | 9/1968 | Skeggs et al. | 23/253 X |
| 3,871,825 | 3/1975 | Liemgburger et al. | 23/230 B |
| 3,901,654 | 8/1975 | Gross | 23/230 B |
| 3,935,074 | 1/1976 | Rubenstein et al. | 23/230 B |
| 3,992,516 | 11/1976 | Lim | 424/8 |
| 3,996,345 | 12/1976 | Ullman et al. | 23/230 B |
| 3,998,943 | 12/1976 | Ullman | 23/230 B |
| 4,018,884 | 4/1977 | Cleeland, Jr. et al. | 424/8 X |
| 4,036,946 | 7/1977 | Kleinerman | 424/8 |

Primary Examiner—R. E. Serwin
Attorney, Agent, or Firm—Eric P. Schellin

[57] ABSTRACT

Aminoglycoside antibiotics, especially gentamicin, in biological fluid samples are assayed fluorimetrically by mixing the sample with a fluorescent-labelled compound and with antibodies. The fluorescence of the compound is reduced when the compound binds with the antibodies, and by measuring the fluorescence of the mixture, the amount of antibiotic in the sample can be determined.

12 Claims, 7 Drawing Figures

IMMUNOASSAY FOR GENTAMICIN

This invention is concerned with immunoassays and, more particularly, with a method of assaying gentamicin and similar aminoglycoside antibiotics in biological fluid samples.

Gentamicin is one of the most important of the aminoglycoside class of antibiotics. It has the structure:

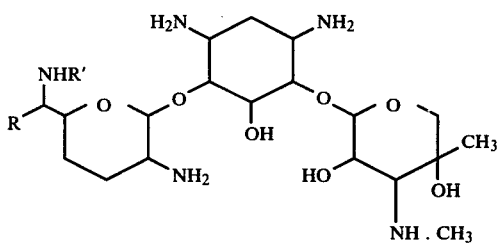

Gentamicin $C_1$: R = R' = Me
Gentamicin $C_2$: R = Me, R' = H
Gentamicin $C_{1a}$: R = R' = H Gentamicin preparations normally consist of a mixture of these components.

Gentamicin is dangerously toxic, particularly towards the ears (ototoxicity), when present in the circulation at as little as 2–3 times the optimum therapeutic level. Furthermore, gentamicin clearance rates from the blood vary widely from patient to patient. It is essential, therefore, that clinical administration of gentamicin be followed in each individual case by monitoring of blood for gentamicin level. Currently the most common assay for gentamicin is a bioassay in which the ability of a blood sample to inhibit the growth of bacteria is estimated. This procedure is slow, imprecise and capable of only a very low throughput of samples. It is almost certain that these problems are at present restricting the clinical use of gentamicin.

Recently, radioimmunoassays (RIA) for gentamicin have been developed and reported in the literature. These are faster and have greater precision than the bioassay procedure, and have the additional advantage of immunospecificity. Disadvantages of the RIA are, firstly, the usual radiation hazards, limited life of lable, and necessity for radioactive counting facilities. Secondly, the necessity for a separation step to isolate the free or antibody-bound labelled fraction for quantitation. Thirdly, the problem of radio-labelling of gentamicin. Tritiated ($^3H$-) gentamicin, obtainable to order commercially, is known to be impure, and use of the tritium label requires expensive liquid scintillation counting methods. The advantages of radio-iodine labelling (e.g. simple gamma-counting quantitation) can only be realised either by first coupling gentamicin to a suitable carrier species, followed by radio-iodination of the carrier, or by coupling or reacting gentamicin with a previously iodinated carrier. These are complex procedures which often show poor reproducibility.

We have now devised an immunoassay procedure for gentamicin and other similar aminoglycoside antibiotics, which does not involve the use of radio-active materials and has a number of advantages over the bioassay procedure referred to above. In particular, we have found that if these aminoglycoside antibiotics are labelled with a fluorescent group, such as fluorescein, the fluorescence of the label is reduced when the antibiotic is treated with specific antibody. As a result, it is possible reliably and effectively to assay biological fluid samples for these antibiotics by determining the fluorescence.

According to the invention, there is provided a method of assaying a biological fluid sample for gentamicin or a similar aminoglycoside antibiotic, which comprises forming a mixture of the sample, a fluorescent-labelled compound (as herein defined) and antibody (e.g. antiserum or immunoglobulins from antiserum) against the antibiotic under assay and the said compound, and measuring the fluorescence of the mixture so formed and thereby determining the amount of aminoglycoside antibiotic present in the sample.

By "fluorescent-labelled compound" we mean a compound which carries a fluorescent group, the fluorescence of which is reduced when the compound binds with the antibody. Thus, the fluorescence of the mixture will be less than the fluorescence of the labelled compound by an amount depending on the quantity of aminoglycoside antibiotic present in the original sample. By measuring the fluorescence of the mixture and comparing it, for example, with a standard curve (described in more detail below) the amount of aminoglycoside antibiotic can be determined.

The fluorescent-labelled compound has to be capable of complexing with the antibody used in the method, and the antibody must also be capable of complexing with the gentamicin (or other similar drug) under analysis. It follows, therefore, that the labelled compound must either be of identical structure (apart from the label) to the gentamicin or other drug under assay, or have a very closely similar structure, since otherwise it will not bind with the antibody. Thus, the labelled compound to be used in the assay of a drug A will either be A itself carrying a fluorescent label, or a compound which is very similar to A (and which carries a fluorescent label).

It is not essential in the method of the invention to use antibody which have been raised using either the particular drug under assay or (where applicable) the closely related compound which is to carry the fluorescent label. The antibody can, instead, be raised using another material, but this will necessarily be closely similar in structure to the drug under assay and to the label compound, since otherwise the antibody will not bind with these two materials.

Some of the aminoglycoside antibiotics are of very closely similar chemical structure, and we have found that, for example, rabbit anti-gentamicin antiserum will bind not only with gentamicin but also with sisomycin and Schering 20569. Cross-reactions of this type make it difficult to assay a sample containing two or more such antibiotics but, in practice, such assays are rarely required. Normally, the biological fluid sample will contain only one aminoglycoside antibiotic and, in such cases, the possibility of cross-reactions is advantageous. Thus, in order for example to assay, by the method of the invention, for gentamicin, sisomycin or Schering 20569, only one antiserum is needed, e.g. rabbit anti-gentamicin antiserum. Not only does this mean that fewer stocks are required in a clinical laboratory, but also it means that drugs can be assayed for which it is difficult to prepare specific antisera.

In the method of the invention, it is preferred to add the labelled compound to the sample under test, and then to form the mixture with the antibody. Alternatively, the antibody can be mixed with the sample, and the labelled compound then added.

The determination of aminoglycoside antibiotic in the sample from the fluorescence measurement, can conveniently be effected using a standard curve. A standard curve for any particular system (i.e. antibiotic/fluorescent-labelled antibiotic or other compound/antiserum) may, for example, be obtained as follows. Solutions of known concentration of the antibiotic to be assayed are made up in pooled normal serum or a suitable buffer. To each solution is added a constant known amount of fluorescent-labelled antibiotic or other compound and sufficient antiserum to form a solution with a predetermined dilution of antiserum. The fluorescence intensities of the solutions are then measured and a standard curve of fluorescence intensity against the concentration of unlabelled antibiotic is plotted.

Such a curve may then be used in the method of the invention for example as follows. To a known volume of the biological fluid sample (containing the antibiotic to be assayed), which may comprise a buffer, is added the constant known amount of fluorescent-labelled antibiotic or other compound used for preparing the standard curve. An amount of antiserum is then added to provide the dilution thereof used in the standard curve determination. The fluorescence intensity of the resulting mixture is measured and from the standard curve, the amount of antibiotic in the biological fluid sample can be determined.

The method of invention is particularly useful for assay of gentamicin, but it can also be used for other aminoglycoside antibiotics, such as streptomycin, tobramycin, neomycin, kanamycin, amikacin, and the more recently discovered sisomycin and Schering 20569, for example. The chemical formulae of sisomycin and Schering 20569 are:

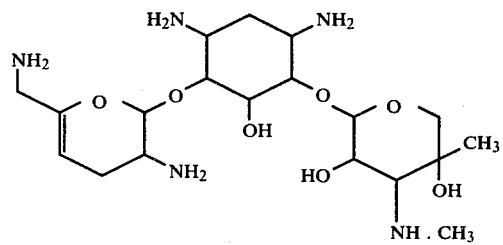

SISOMYCIN

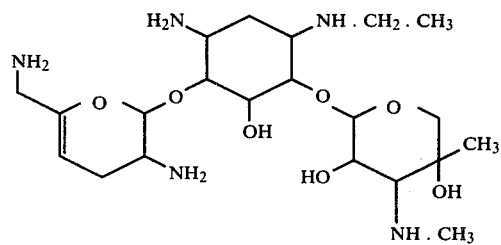

SCHERING 20569

In the assay of gentamicin by the method of the invention, the preferred fluorescent label is fluorescein. This can be attached to gentamicin by, for example, reacting gentamicin with fluorescein isothiocyanate to give fluoresceinthiocarbamyl gentamicin (hereafter "FTC-G"). Other fluorescent groups can also be used, such as for example dansyl, rhodamine, fluorescamine, pyrene and 2-methoxy-2,4-diphenyl-3(2H)-furanone. The suitability of any particular fluorescent group with any particular antibiotic/antiserum system can readily be determined by routine trial and experiment. The fluorescent group should be one which is compatible with the system as a whole to show a reliable and reproducible fluorescent quenching effect upon formation of the labelled antibiotic/antiserum complex.

In this connection, it should be noted that the fluorescent quenching is dependent not only upon the particular fluorescent group used as label, but also upon the nature of the antibiotic and antiserum. The latter must also be selected having regard to its suitability in the overall system. Again, routine trial and experiment will reveal the suitability or otherwise of a particular antiserum in a particular antibiotic/fluorescent-labelled antibiotic system. We have found that with gentamicin labelled with fluorescein, rabbit antisera produced by injecting gentamicin coupled to bovine serum albumin by the carbodiimide method are satisfactory.

In the particular case of gentamicin/FTC-G/rabbit antiserum, we believe that fluorescent quenching occurs by inter-action between the fluorescent label and groups of the antibody molecule.

It will be appreciated that the method of the invention includes the so-called "competitive binding" technique, in which there is competition between the labelled and unlabelled antigen (antibiotic) to bind with a limited amount of antibody (antiserum). Competitive binding immunoassays are very well known, and normally necessarily involve separation of the bound antibody:antigen complexes from free antigen. This separation step (which is, for example, necessary in RIA) is a practical inconvenience. The method of the present invention, however, does not involve any separation step, and this makes the method ideally suited to analyses of the continuous-flow type. Accordingly, the invention includes the method herein described effected in a continuous-flow manner, and also apparatus therefor.

In continuous flow analyses according to the present invention, the mixture of sample, antibody and fluorescent labelled compound, is passed along a conduit and the fluorescence is measured. In a preferred procedure, which is described in U.S. patent specification no. 2,797,149, individual segments of mixture are passed sequentially along the conduit, separated by an inert fluid segment (e.g. air) and, if desired, a wash liquid segment. The mixture can be formed in the conduit itself, by supplying to the conduit, in phase with segments of components of the mixture already present therein, the one or more further components, mixing of the components occurring in the conduit as the mixture flows therethrough.

It is a highly advantageous feature of the present invention that analyses of the drugs in question can be carried out relatively simply in this continuous flow manner, mainly as a result of the fact that no separation step is required in the method of the invention. Thus, the mixture flowing in the conduit may be passed directly to (or through) a fluorescence cell for direct measurement. It is therefore possible by the method of the invention to assay these particular drugs on a continuous flow basis which has been hitherto impossible or very difficult by prior known assay techniques.

Among the advantages of the present invention are the following:
1. FTC-G is readily prepared in excellent yield from easily available and cheap starting products.
2. FTC-G has good shelf-life.
3. Neither radiation hazard nor the need for radioactive counting facilities is involved.
4. No separation step is needed.
5. Measurement is by conventional fluorimetry.
6. Because of points 4 and 5, the procedure can be automated easily.
7. The assay is very fast. Only a few minutes are necessary for attainment of immunological equilibrium between antibody, FTC-G and gentamicin, after which a single fluorescence measurement gives the result.
8. The assay can be immunospecific for the particular antibiotic, subject to the comments made above concerning cross-reactions.
9. The serum sample size required is very small. 5 $\mu$l or less suffices for a discrete assay.

In order that the invention may be more fully understood, the following Examples are given by way of illustration only.

EXAMPLES

EXAMPLE 1. Preparation of fluorescein-labelled gentamicin (FTC-G)

Figure 1:
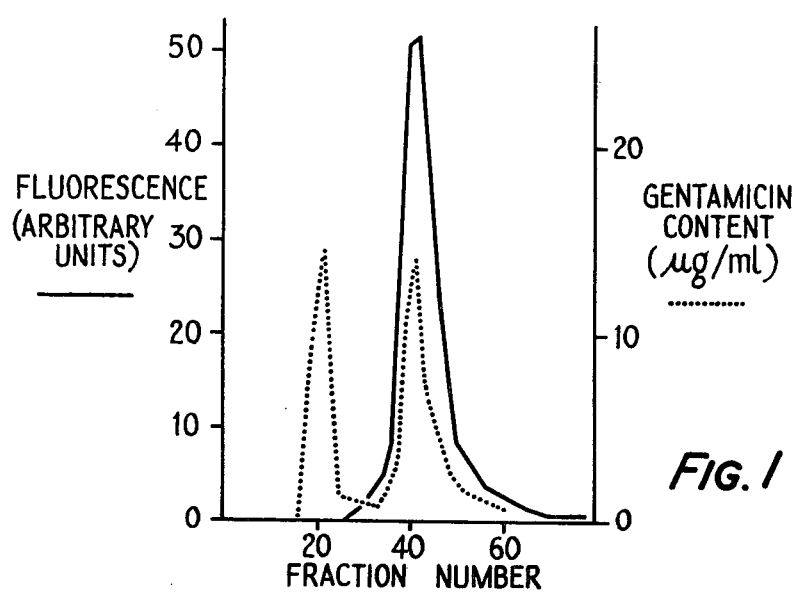
FIG. 1 is a graph which shows the result of analyzing Gentamicin (1 mM) with fluorescein isothiocyanate (1.25 mM) in 0.05M sodium carbonate/bicarbonate buffer, pH 9.0.

Gentamicin (1mM) and fluorescein isothiocyanate (FITC) (1.25mM) were allowed to react in 0.05M sodium carbonate/bicarbonate buffer, pH 9.0, for 2 hours at room temperature. 2ml of the reaction mixture was applied to a column (1 × 97cm) of G-15 grade Sephadex and eluted with carbonate/bicarbonate buffer as above, with a flow rate of 1.8ml/h. Column fractions (1.8ml) were assayed for gentamicin content by radioimmunoassay and for fluorescein content by fluorimetry. FIG. 1 of the accompanying drawings shows the result. Unreacted gentamicin left the column first. The FTC-G product exited next, well separated from the gentamicin peak. Unreacted FITC was very strongly held on the G-15 column and was not eluted.

The FTC-G product was stored in solution, either frozen or at 4° C. Electrophoretic characterisation showed the presence of one major band (presumed to be mono-FTC-labelled gentamicin) and two minor bands (presumed to be poly-FTC-labelled gentamicin).

Concentrations of FTC-G quoted below are based on the gentamicin content as assessed by radio-immunoassay.

EXAMPLE 2. Preparation of anti-gentimicin sera

Rabbits were immunised with gentamicin coupled to bovine serum albumin by means of the carbodiimide method.

Figure 2:
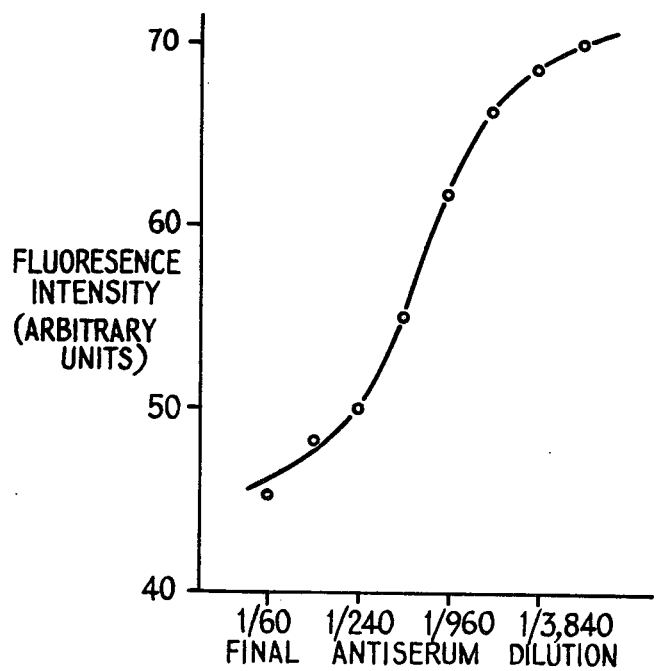
FIG. 2 is a graph which shows fluorescence intensity of fluoresceine isothiocyanate-gentamicin plotted against a series of antibody dilutions.

EXAMPLE 3. Fluorescence quenching immunoassay for gentamicin (i) Antibody dilution curve In order to choose optimum assay conditions, 0.5ml amounts of a 16.4ng/ml solution of FTC-G in 0.1M sodium phosphate buffer pH 7.5 were added to doubling dilutions (1ml) of an antiserum in the same buffer. After allowing a few minutes for equilibration, fluorescence intensity was measured (see FIG. 2 of the accompanying drawings). From this curve, a final antibody dilution of 1/240 in 1.5ml was chosen for construction of the standard curve.

(ii) Standard curve

Figure 3:
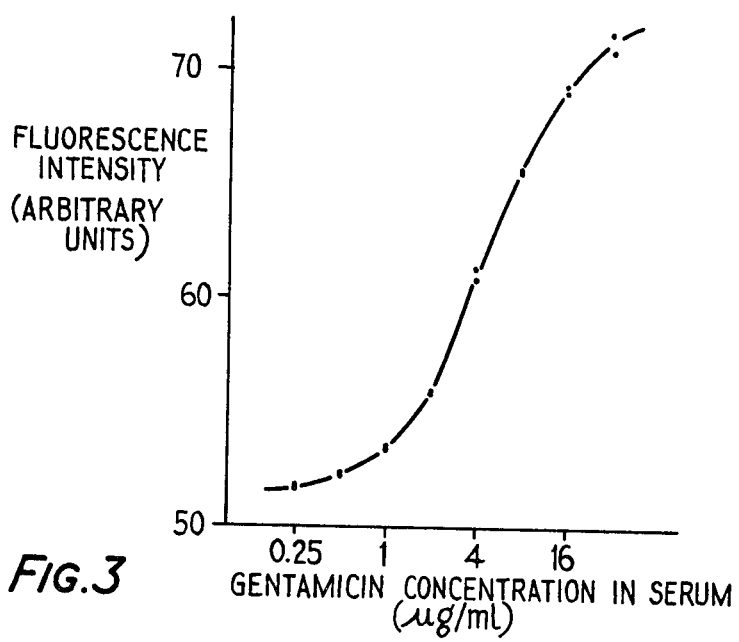
FIG. 3 shows a standard curve of fluorescence-intensity for fluoresceine isothiocyanate-gentamicin using known concentrations of gentamicin in serum.

Gentamicin was added in known amounts to pooled normal human serum. Aliquots of these standard samples were diluted 1/50 in 0.1M sodium phosphate buffer pH 7.5. To 0.5ml of the diluted standard samples was added 0.5ml of a 16.4ng/ml solution of FTC-G in the same buffer, followed by 0.5ml of antiserum diluted 1/80 in the same buffer. After allowing a few minutes for equilibration, the fluorescence intensity of the assay mixtures was measured. The contribution of the intrinsic fluorescence of the pooled normal human serum to the total fluorescence intensity of the assay mixtures was estimated independently by adding 1ml of the phosphate buffer to 0.5ml of the diluted standard samples and measuring the fluorescence. By subtraction of the serum intrinsic fluorescence intensity from the total intensity of the assay mixtures, the standard curve shown in FIG. 3 was produced.

EXAMPLE 4. Assay of gentamicin in patient samples

Serum samples from patients receiving gentamicin therapy were assayed according to the procedure described in Example 3, section (ii). The contribution of the intrinsic fluorescence of each serum sample, measured independently, was subtracted from the total fluorescence intensity of the corresponding assay mixture, and the result used to determine, from an appropriate standard curve, the amount of gentamicin in the serum sample.

Figure 4:
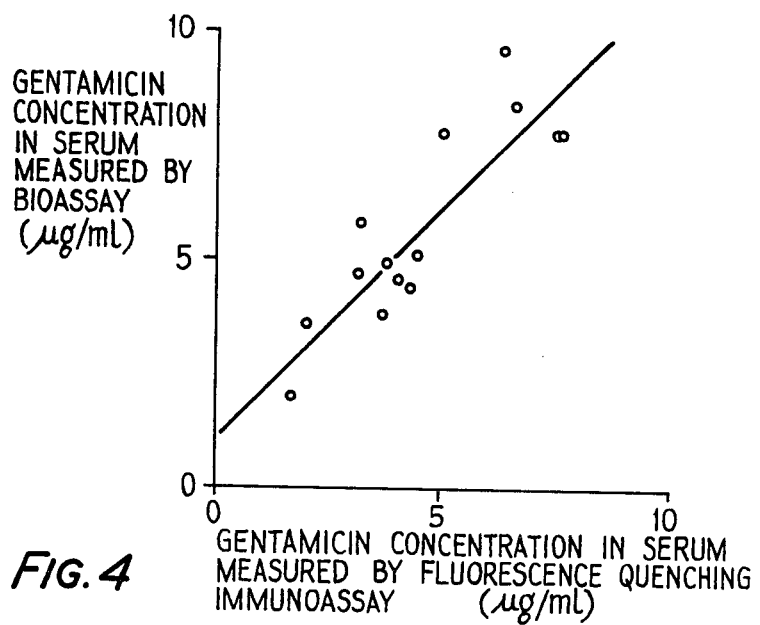
FIG. 4 is a graph which shows the relationship of gentamicin concentration in serum measured by bioassay to gentamicin concentration in serum measured by fluorescence quenching.

FIG. 4 shows the correlation between gentamicin levels measured by fluorescence quenching immunoassay, and levels measured by an independent laboratory using an established bioassay. The computed line of best fit is shown. Given the acknowledged inaccuracy of the bioassay technique, the agreement between the two methods is acceptable, and satisfactory for clinical purposes.

EXAMPLE 5. Continuous-flow system for automated assay of gentamicin

Figure 5:
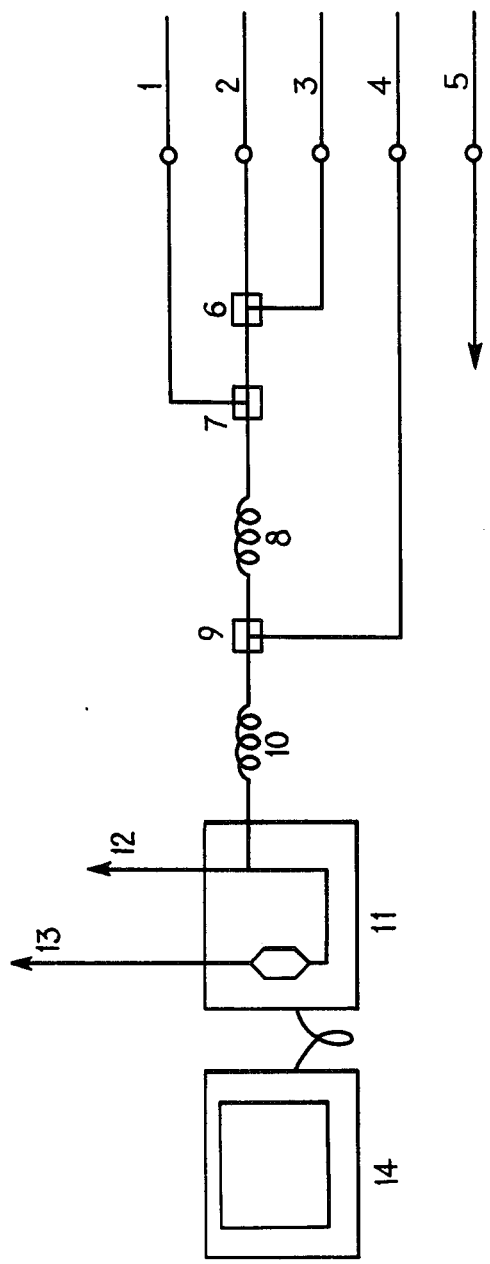
FIG. 5 shows a form of flow system suitable for a continuous flow analysis according to the method of the present invention.

FIG. 5 of the accompanying drawings shows one form of flow system, suitable for a continuous-flow analysis. The system comprises sample input line 1, FTC-G input line 2, air input line 3 and antiserum input line 4. Lines 2 and 3 meet at segmenter 6 which is connected to junction 7 where line 1 joins line 2. Downstream of junction 7 line 2 is provided with a mixing coil 8 and then passes to junction 9 where line 4 joins. Downstream of 9 is a mixing coil 10 and finally a fluorimeter 11 having a waste outlet 12 and an outlet 13 downstream of the fluorescence cell connected to line 5 and thence to waste. The fluorimeter 11 is operatively coupled to recorder 14.

In operation, a controlled amount of FTC-G enters line 2 and is segmented by air in segmenter 6. The sample to be tested (e.g. serum), diluted as necessary, is introduced into the segmented stream in junction 7, followed by mixing in coil 8, then a controlled amount of antiserum is introduced in junction 9, followed by mixing in coil 10 before passing to fluorimeter 11.

EXAMPLE 6. Automated assay of gentamicin: standard curve

Gentamicin was added in known amounts to pooled normal human serum. Aliquots of these standard samples were diluted 1/100 in 0.1M Tris/HCl buffer pH 7.5 containing 10mM $MgCl_2$ ("Tris/$MgCl_2$ buffer"). Using the flow system of FIG. 5, a standard curve was produced by means of the following procedure.

Figure 6:
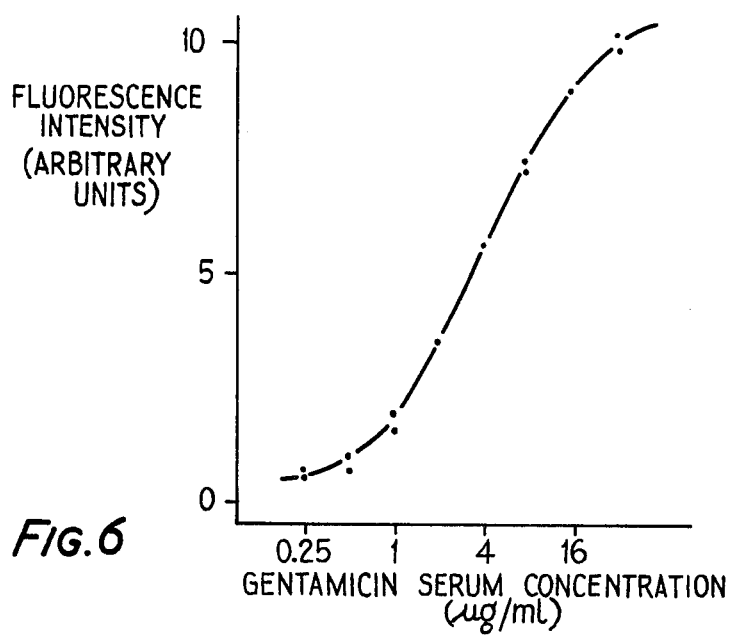

The standard samples were pumped through input line 1 at 0.16ml/min. Each sample was pumped for 1 min, then Tris/$MgCl_2$ buffer was pumped for a 1 min wash period before pumping of the next sample. FTC-G, 8.2ng/ml in Tris/$MgCl_2$ buffer containing 0.1% V/V Triton X-100 detergent, was pumped through input line 2 at 0.16ml/min. Antiserum, diluted 1/160 in Tris/$MgCl_2$ buffer containing 0.1% V/V Triton X-100 detergent, was pumped through input line 4 at 0.16ml/min. The mixed streams were pulled through the fluorimeter flow cell at 0.42ml/min (line 5). The total fluorescence intensity of the mixed streams was recorded on the chart recorder. The intensity recorded during the wash periods (corresponding to maximum binding of FTC-G to antiserum in absence of sample) was subtracted from the intensity recorded during passage of each assay mixture through the fluorimeter flow cell. In this way, the net increase in fluorescence intensity due to each sample was measured. When the standard samples had passed through the system, the solution pumped through lines 2 and 4 was changed to Tris/$MgCl_2$ buffer containing 0.1% V/V Triton X-100 detergent. The standard samples were then re-run through the system. The intrinsic fluorescence intensity of the standard serum samples was thereby measured. By subtraction of the serum intrinsic fluorescence intensity from the net fluorescence intensity increase measured for each assay mixture, the standard curve shown in FIG. 6 was produced.

EXAMPLE 7. Automated assay of gentamicin in patient samples

Serum samples from patients receiving gentamicin therapy were assayed according to the procedure described in Example 6. The contribution of the intrinsic fluorescence of each serum sample, measured independently, was subtracted from the net fluorescence intensity increase measured for the corresponding assay mixture, and the result used to determine, from an appropriate standard curve, the amount of gentamicin in the serum sample.

Figure 7:
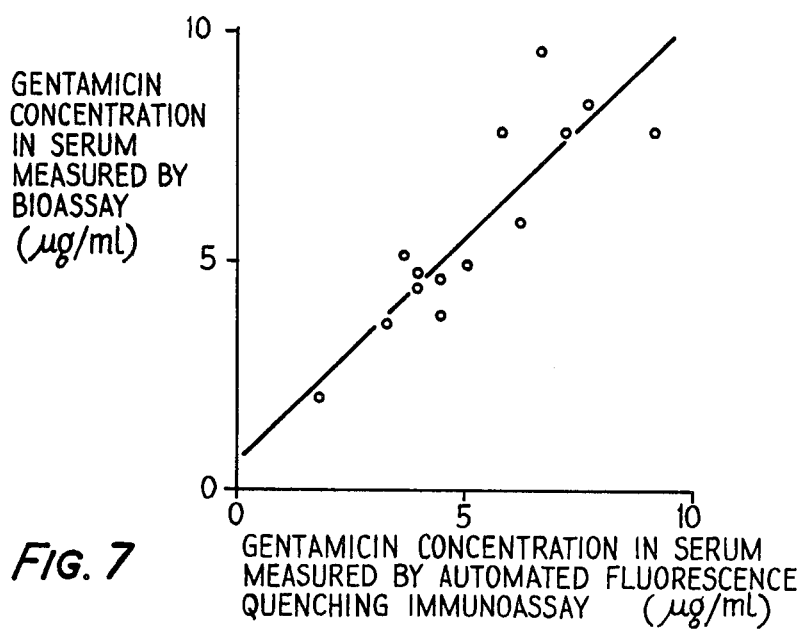

FIG. 7 shows the correlation between gentamicin levels measured by automated fluorescence quenching immunoassay, and levels measured by an independent laboratory using an established bioassay. The computed line of best fit is shown. Given the acknowledged inaccuracy of the bioassay technique, the agreement between the two methods is acceptable, and satisfactory for clinical purposes.

I claim:

1. A method of assaying a biological fluid sample for an aminoglycoside antibiotic comprising:
   a. forming a mixture of the sample, a fluorescent-labelled compound, the fluorescence of which is reduced when the compound binds with antibodies, and antibody against the antibiotic under assay and the compound;
   b. measuring the fluorescence of the mixture to determine the amount of reduction of fluorescence of the compound to determine the amount of aminoglycoside antibiotic present in the sample.

2. A method according to claim 1 wherein the antibiotic is gentamicin

3. A method according to claim 2 wherein the fluorescent-labelled compound is fluorescein-labelled gentamicin.

4. A method according to claim 3 wherein the fluorescein-labelled gentamicin is fluoresceinthiocarbanyl gentamicin.

5. A method according to claim 2 wherein the antibody is rabbit anti-gentamicin antiserum.

6. A method according to claim 1 which is carried out in a continuous-flow manner.

7. A method according to claim 1, wherein segments of the mixture are flowed along a conduit, separated by segments of an inert fluid, and the fluorescence of the mixture segments is measured without any step of separation of reaction product from the mixture.

8. A method according to claim 7 wherein the fluorescence of the mixture segments is compared with standard results to determine the amount of aminoglycoside antibiotic under assay in the sample.

9. A method according to claim 8 wherein segments of the said mixture are separated by segments of air.

10. A method of assaying a biological fluid sample for an antibiotic selected from gentamicin, sisomycin, Schering 20569, streptomycin, tobramycin, neomycin, kanamycin and amikacin, which comprises forming a mixture of:
    a. the sample;
    b. a fluorescent-labelled compound which is a compound which carries a fluorescent group, the fluorescence of which is reduced when the compound binds with antibody; and
    c. antibody against the antibiotic and the fluorescent-labelled compound measuring the fluorescence of the mixture; comparing the said fluorescence with standard results and thereby determining the amount of said antibiotic present in the sample.

11. A method according to claim 10 which is carried out in a continuous-flow manner.

12. Apparatus for continuous-flow analysis of a biological fluid sample for an aminoglycoside antibiotic by a fluorescent-quenching method, which apparatus comprises a conduit; means for flowing along the conduit a mixture of the sample and a fluorescent-labelled compound, the fluorescence of which is reduced when the compound binds with antibody, and antibody against the antibiotic and the fluorescence of the mixture; and means for comparing the fluorescence of the mixture with standard results to determine the amount of antibiotic under assay in the sample.

* * * * *